United States Patent
Liu et al.

(10) Patent No.: US 6,730,031 B2
(45) Date of Patent: May 4, 2004

(54) EDITING AND TRIMMING APPARATUS AND METHOD FOR EXTENDED FIELD OF VIEW ULTRASONIC IMAGING SYSTEMS

(75) Inventors: Lingnan Liu, Mill Creek, WA (US); Lars Jonas Olsson, Woodinville, WA (US)

(73) Assignee: Koninklijke Philips Electronics, N.V. (NL)

( * ) Notice: Subject to any disclaimer, the term of this patent is extended or adjusted under 35 U.S.C. 154(b) by 0 days.

(21) Appl. No.: 09/960,761

(22) Filed: Sep. 21, 2001

(65) Prior Publication Data

US 2002/0045825 A1 Apr. 18, 2002

Related U.S. Application Data

(63) Continuation-in-part of application No. 09/345,243, filed on Jun. 30, 1999, now Pat. No. 6,238,345.

(51) Int. Cl.$^7$ .................................................. A61B 8/00
(52) U.S. Cl. ......................................................... 600/443
(58) Field of Search .................................... 600/437, 440, 600/441–447, 449–459; 382/154; 345/473; 348/36; 367/7, 11, 130, 138; 73/625, 626; 128/916

(56) References Cited

U.S. PATENT DOCUMENTS

| | | | |
|---|---|---|---|
| 4,463,763 A | 8/1984 | Koyano et al. | 128/661 |
| 5,538,004 A | 7/1996 | Bamber | 128/662.06 |
| 5,566,674 A | 10/1996 | Weng | 128/660.07 |
| 5,575,286 A | 11/1996 | Weng et al. | 128/653.1 |
| 5,645,066 A | 7/1997 | Gandini et al. | 128/660.07 |
| 5,671,745 A | 9/1997 | Park et al. | 128/660.07 |
| 5,782,766 A * | 7/1998 | Weng et al. | 600/443 |
| 5,899,861 A | 5/1999 | Friemel et al. | 600/443 |
| 5,910,114 A | 6/1999 | Nock et al. | 600/437 |
| 6,102,865 A | 8/2000 | Hossack et al. | 600/459 |
| 6,117,081 A * | 9/2000 | Jago et al. | 600/443 |
| 6,238,345 B1 | 5/2001 | Wissler et al. | 600/443 |
| 6,283,917 B1 * | 9/2001 | Jago et al. | 600/437 |
| 6,416,477 B1 * | 7/2002 | Jago | 600/447 |

FOREIGN PATENT DOCUMENTS

WO 00/24316 5/2000

\* cited by examiner

*Primary Examiner*—Ali M Imam
(74) *Attorney, Agent, or Firm*—Dorsey & Whitney LLP

(57) ABSTRACT

An ultrasound imaging system acquires a sequence of partially overlapping image frames, and stores data corresponding to the image frames in a image frame buffer. The relative spatial positions of the image frames are determined by a correlator, and the resulting spatial position data are then stored in an extended image memory and a history buffer along with data corresponding to the image frames. The data stored in the extended image memory and the history buffer can then be used to generate a panoramic image, which is displayed by the imaging system. Significantly, the data corresponding to the image frames are retained in the image frame buffer after the panoramic image has been displayed so that specific image frames can be excluded from the data corresponding to the panoramic image to either edit defective image frames from the panoramic display or to trim the boundaries of the panoramic display.

39 Claims, 6 Drawing Sheets

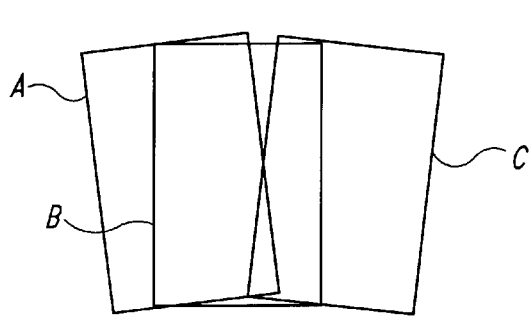
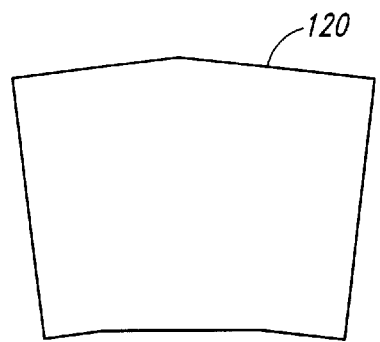
Fig. 4A          Fig. 4B
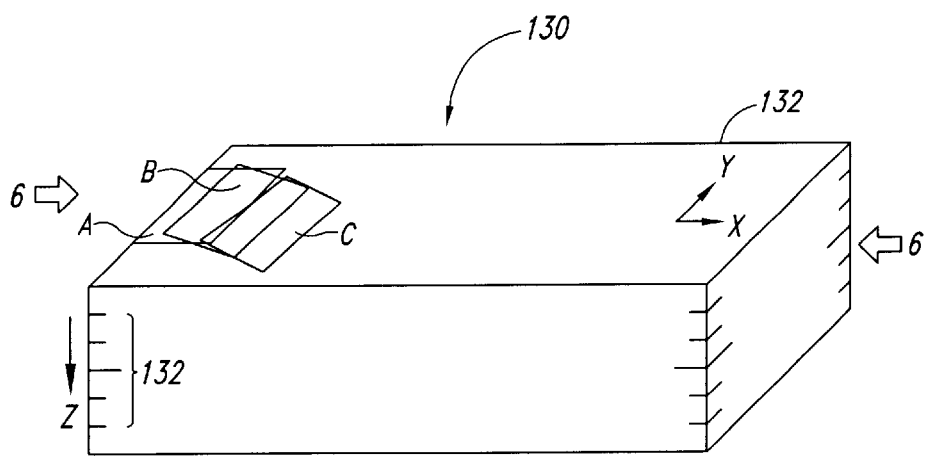
Fig. 5

EDITING AND TRIMMING APPARATUS AND METHOD FOR EXTENDED FIELD OF VIEW ULTRASONIC IMAGING SYSTEMS

RELATED APPLICATION

This is a continuation-in-part application of U.S. patent application Ser. No. 09/345,243, filed Jun. 30, 1999, now U.S. Pat. No. 6,238,345.

TECHNICAL FIELD

This invention relates to ultrasonic diagnostic imaging systems and, in particular, to a method and apparatus for editing and trimming individual frames from which an extended field of view ultrasonic image is composed.

BACKGROUND OF THE INVENTION

Significant effort has been devoted to extending the field of view of ultrasound images so that a larger area of tissues and organs could be viewed in a single image. Early extended field of view ("EFOV") imaging systems, known as "B-arm scanning systems," included a single beam ultrasound transducer mounted at the end of an articulated arm. The joints of the articulated arm contained sensors that produced an electrical signal indicative of the spatial position of the transducer. As the transducer was scanned over the body of the patient, a scan line was produced from the ultrasound returns obtained from the transducer and the relative spatial locations of the transducer while the returns were being obtained. The scan lines from multiple adjacent scans of the transducer were computed and stored, and then assembled in consecutive, side-by-side locations to create an EFOV or "panoramic" image. These early EFOV systems were thus capable of generating an ultrasonic image that could laterally extend for the maximum number of successive scan lines that the system could store and display and over the range of positions that arm could extend.

In recent years electronically scanned array transducers have been adapted for the same purpose. Since an electronically scanned array transducer automatically produces a two dimensional image, movement of the array transducer in the plane of the image will produce successive, spatially offset two dimensional images. Each new image or "image frame" in a new spatial location can be spatially registered with a previously acquired image frame that it overlaps, then combined with the previous image frames to produce an EFOV or panoramic image that is laterally extensive in the direction of motion of the array transducer. In some commercially available panoramic imaging systems, more than 80–90 percent of each image frame overlaps an adjacent image frame. The extent of the panoramic image is determined by the capacity of the ultrasound system to store and display multiple partially overlapping two dimensional images.

Prior art panoramic imaging systems are capable of producing a continuous panoramic image as a scanhead is continually moved in a given direction along the surface of the body. In such systems, the EFOV or panoramic image is generated in real time from image frames as the image frames are being acquired. However, a clinician acquiring a panoramic image in this manner is often trying to image a structure of extended length in the body, such as a blood vessel in an arm or leg. Although the clinician is trying to maintain the vessel in alignment with the image plane of the scanhead, frequently the path of the vessel and the moving scanhead will move out of alignment and the vessel will no longer appear in the image. In such circumstances, the usual recourse is to repeat the scan from the beginning, thereby unduly extending the time required to acquire the panoramic image. To solve this problem, a system described in U.S. patent application Ser. No. 09/345,242 to Roy B. Peterson et al. entitled "EXTENDED FIELD OF VIEW ULTRASONIC IMAGING DIAGNOSTIC IMAGING WITH IMAGE REACQUISITION," which is incorporated herein by reference, allows the clinician to compensate for the premature termination of the scan by being able to reacquire the blood vessel in the EFOV image. In operation, newly acquired image frames may be obtained for an EFOV image by moving the scanhead in either direction. Thus, if the scanhead moves such that structure of interest is out of the scan plane of the EFOV image, the clinician may reverse the direction of the scan until the structure is reacquired in a new image frame, preferably at the point at which it initially disappeared from view. The resulting panoramic image is then composed of the original image frames and the repeated image frames. The clinician can therefore recover from misalignment of the structure of interest and the scan plane and continue the scan without having to restart the scan from the beginning.

Although the system described in the above-identified application to Peterson et al. is primarily designed to reacquire a vessel or tissue of interest, it can also be used to repeat image frames that contain defects that would impair the usefulness of the resulting panoramic image. For example, the clinician may inadvertently lift the scanhead from the skin during a scan, particularly at or toward the end of the scan. Lifting the scanhead in this manner causes phenomena known as "flash artifact" in which all or a portion of the image frame is seriously blurred. Flash artifact may also be caused by other defects in individual frames. If an image frame exhibiting flash or any other image artifact is combined with other image frames to produce a panoramic image, the panoramic image may be seriously degraded in the area in which the image frame exhibiting flash artifact was used.

Although the above-described system allows defects in an image to be corrected without repeating the entire scan, the defects must be noticed and corrected in real time as the image is being obtained. If the defect is not noticed until the entire panoramic image has been obtained, the entire scan must be repeated to obtain an entirely new panoramic image. Furthermore, since the panoramic image is created by the image frames as the image frames are being obtained, it is not possible to improve or enhance the panoramic image by subsequently processing or eliminating individual image frames.

There is therefore a need for a system and method for allowing image frames to be individually examined during or after the image frames making up a panoramic image have been obtained so that the individual image frames can be eliminated from the image frames that have been combined to produce the panoramic image.

SUMMARY OF THE INVENTION

A panoramic ultrasound imaging system and method in accordance with the invention acquires ultrasound image frames in a conventional manner. However, instead of simply combining the image frames to produce a panoramic image, data corresponding to the individual image frames are saved in a frame memory, and the data are retained after the image frames have been combined to create the panoramic image. As a result, defects in the panoramic image created by flash and other artifacts in an individual image frame can be removed by simply re-creating the panoramic image from all of the stored image frames except the image frames exhibiting artifacts. In addition to editing the panoramic image in this manner, the panoramic image can be trimmed at either end by eliminating portions of individual image frames extending beyond a specific line. The individual image frames my be examined for artifacts either manually or automatically using predetermined criteria, and they may be examined to edit the panoramic image either after all of the image frames have been combined to create the panoramic image or in real time as the image frames are being obtained.

BRIEF DESCRIPTION OF THE DRAWINGS

FIGS. 4a and 4b are schematic views illustrating the manner in which three overlapping image frames are combined to form a panoramic image.

FIG. 5 is a schematic view depicting the organization of an extended field of view history buffer used in the extended field of view image processor of FIG. 3.

DETAILED DESCRIPTION OF THE INVENTION

Figure 1:
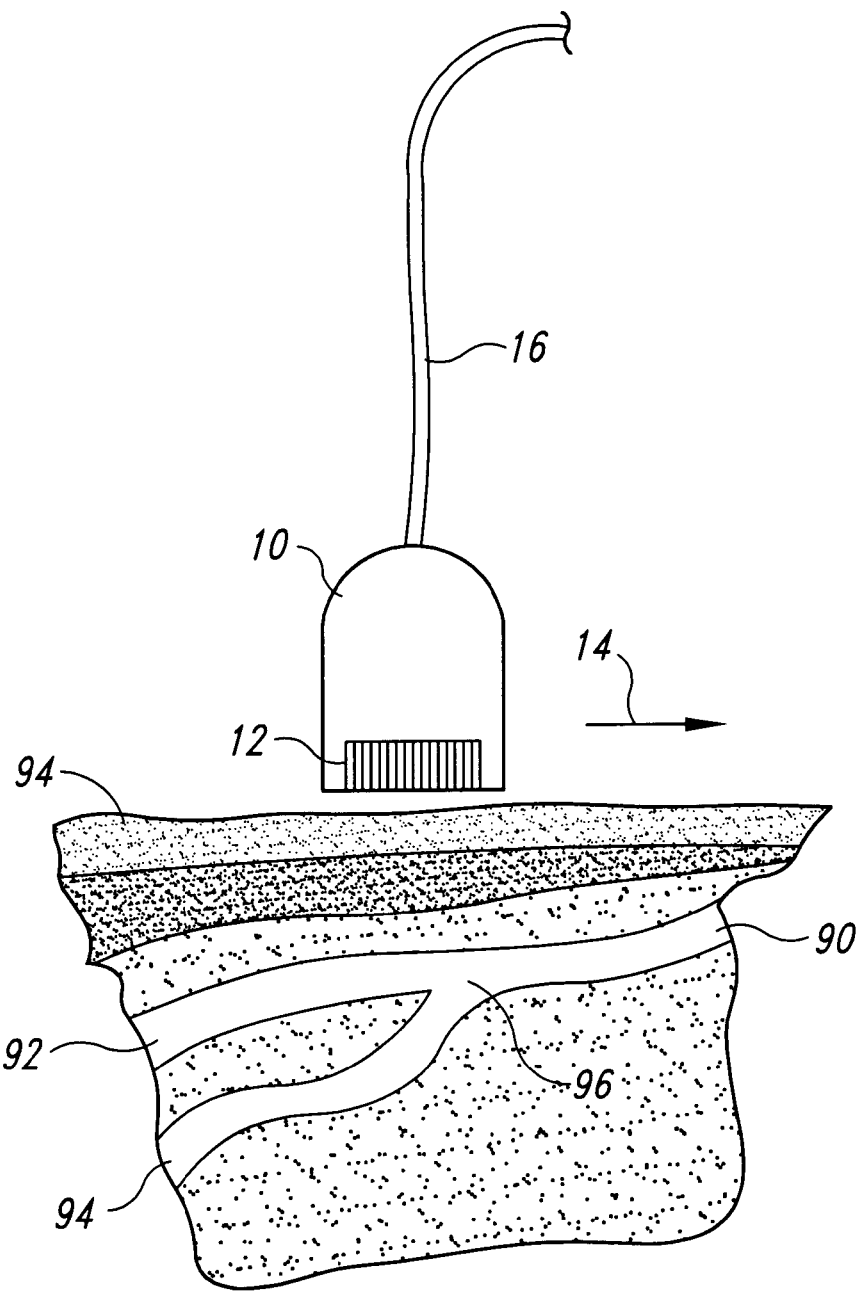
FIG. 1 is a schematic view illustrating a technique for scanning an array transducer to produce an extended field of view image in accordance with one embodiment of the invention.

One technique for scanning an array transducer to produce an extended field of view or panoramic image is shown in FIG. 1. An ultrasonic scanhead 10, which includes an electronically scanned array transducer 12, is shown in contact with a skinline 94 of a patient. The ultrasonic scanhead 10 is coupled to an imaging system (not shown in FIG. 1) by a cable 16. In this example, the clinician is scanning a length of blood vessels 90, 92, 94 to display the blood vessels in an extended field of view image. However, it will be understood that the scanhead can likewise be used to scan other blood vessels as well as tissues or organs. As shown in FIG. 1, only the narrow region of a bifurcation 96 in the blood vessels 90, 92, 94 is directly beneath the aperture of the array transducer 12 and hence viewable in a single conventional image. To scan a length of the blood vessels 90, 92, 94, the clinician slides the scanhead 10 in the direction 14, which denotes a direction co-aligned with the longitudinal axis of the array transducer 12 and the plane of an image. As the scanhead 10 is moved in the direction 14, successive planar images referred to herein as image frames are acquired, each being slightly displaced (as a function of the speed of scanhead motion and the image acquisition rate) in the direction 14 from the previous image. As explained in greater detail below, the displacement between successive image frames is computed and the image frames are registered and combined on the basis of the displacements to produce a composite panoramic image of the blood vessels 90, 92, 94.

Ideally, it is desirable for the scanhead 10 to be translated at a constant speed while image frames are being acquired, so that individual image frames are not stretched or compressed relative to frames acquired with different speeds of scanhead motion. It is also desirable for the scanhead 10 to be moved in a single plane so there is high correlation from each image frame to the next. However, manual scanning over an irregular body surface often causes departures from either or both of these desirable conditions. Either or both of these effects of less than desirable manual scanning can be compensated for by conventional means, such as described in the previously cited application to Peterson et al. It will also be understood that image frames can be obtained in accordance with the invention using a scanhead that is structurally different from the scanhead 10 shown in FIG. 1.

Figure 2:
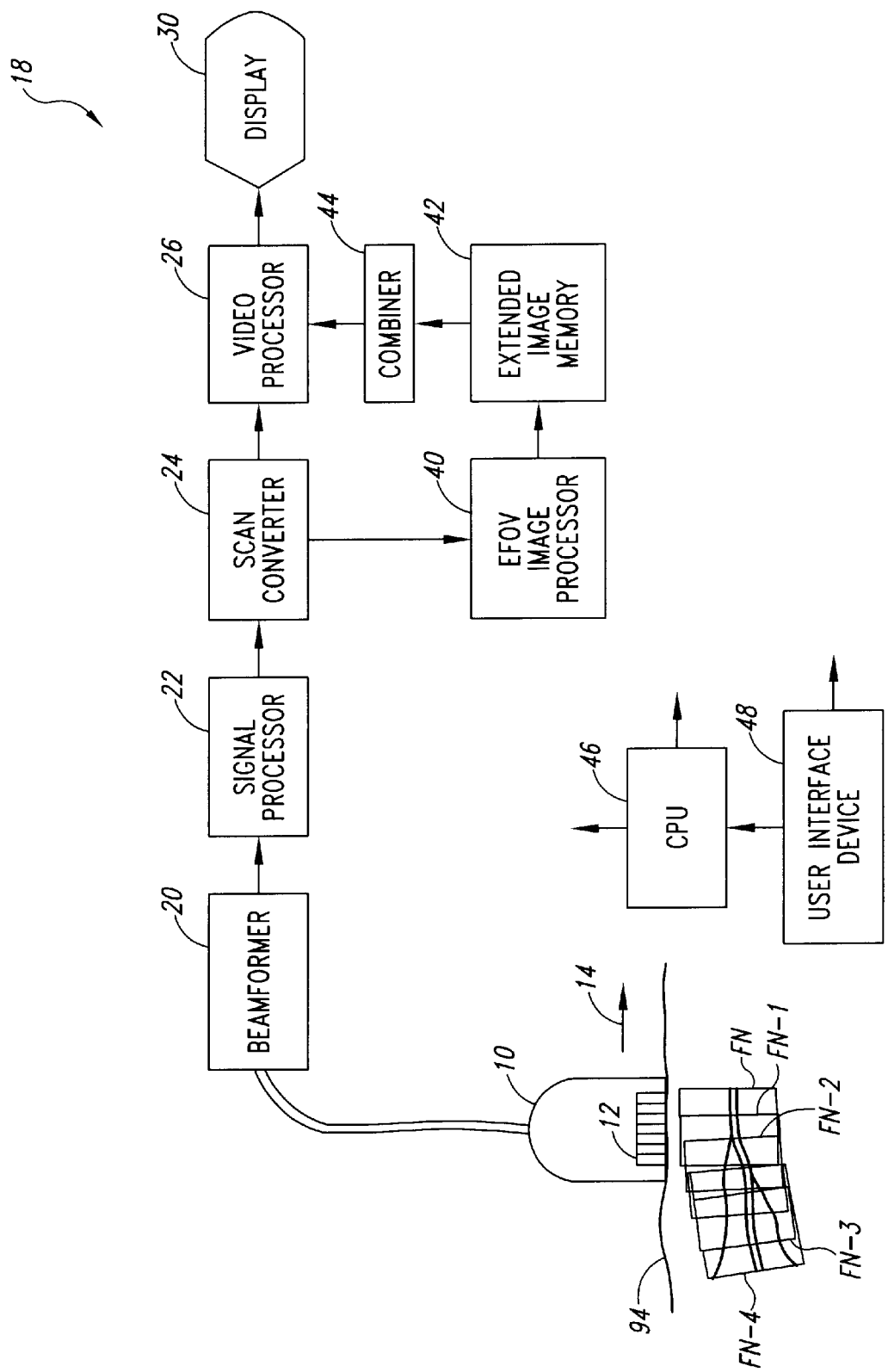
FIG. 2 is a block diagram illustrating a panoramic ultrasonic diagnostic imaging system constructed in accordance with one embodiment of the invention.

One embodiment of an ultrasonic diagnostic imaging system 18 for producing panoramic images in accordance with the principles of the present invention is shown in FIG. 2. The scanhead 10 is assumed to be moving in the direction 14 of the planes of successively acquired images $F_{n-4}$–$F_n$. The acquired images $F_{n-4}$–$F_n$ are transparently shown in this drawing so that their spatial overlap can be appreciated. The first image acquired in this sequence is image frame $F_{n-4}$, and the last image acquired is frame $F_n$, shown in alignment with the aperture of the array transducer 12. Electric signals from the scanhead 10 are coupled through the cable 16 and applied to a conventional beamformer 20, which processes signals corresponding to echoes of each acquired image frame into a beam. The signals corresponding to the beams are then processed by a signal processor 22 of conventional design and arranged in respective ultrasonic image frames by a scan converter 24. To form conventional real time images, each image frame is coupled to a video processor 26 and displayed on an image display 30.

In accordance with one embodiment of the present invention, data corresponding to each image frame is coupled to an EFOV image processor 40. The EFOV image processor 40, which may operate with either estimated data (pre-scan converted) images or display data (scan converted pixel data) images, receives and stores data corresponding to each newly acquired image frame during the EFOV mode of operation and computes the displacement and rotation between the new image frame and the previously acquired image frame of the EFOV image, as more fully described below. The EFOV image processor 40 then combines the data corresponding to image frames into a panoramic image, and stores the panoramic image data in an extended image memory 42, as described below. The panoramic image data stored in the extended image memory 42 is extracted from the memory 42 and combined by a combiner 44 to form a panoramic image, which is coupled to the video processor 26 for viewing on the display 30.

The operation of the imaging system 18 is preferably controlled by a CPU 46, which is coupled to various of the components shown in FIG. 2. A user interface device 48, such as a keyboard, mouse, trackball, or other device, may be manipulated by the clinician to control the operation of the imaging system 18.

Figure 3:
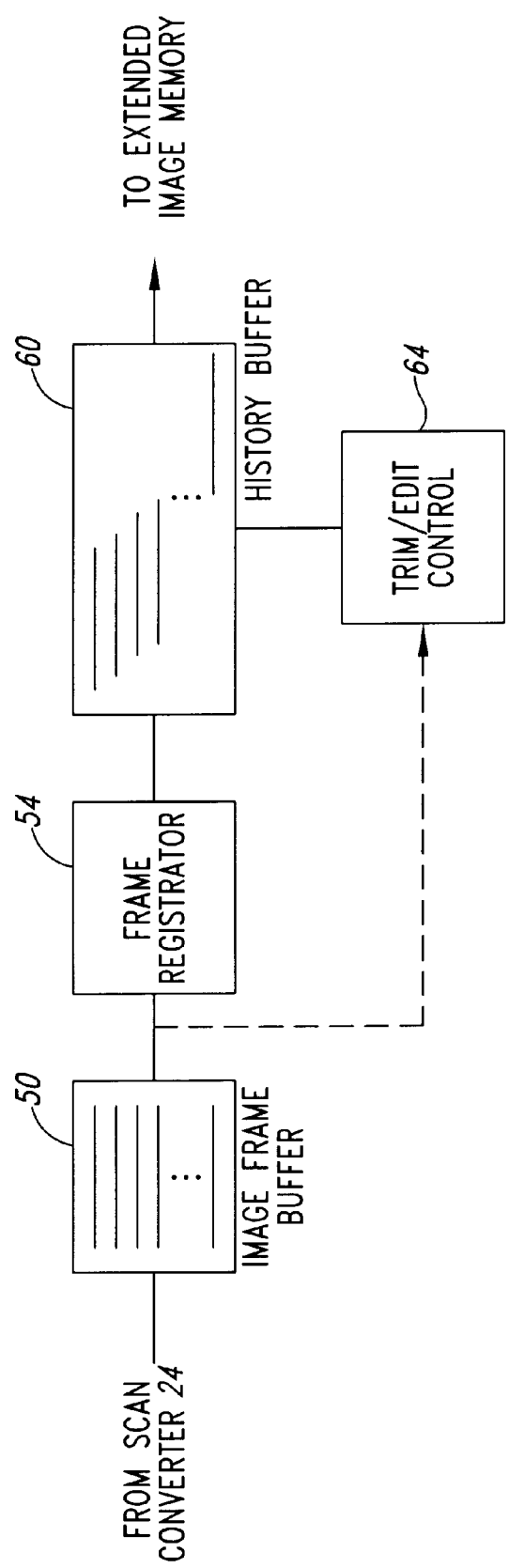
FIG. 3 is a block diagram illustrating one embodiment of an extended field of view image processor used in the panoramic ultrasonic diagnostic imaging system of FIG. 2.

One embodiment of the EFOV image processor 40 in accordance with the invention is shown in FIG. 3. As mentioned previously, data corresponding to each image frame is generated by the scan converter 24 (FIG. 2). This image frame data is applied to and stored in an image frame buffer 50, which may be a dedicated memory, a portion of system memory used by the CPU 46 or some other memory. The image frame buffer 50 stores all of the data corresponding to each image frame in individually accessed blocks of memory so that data for each image frame may be accessed. The individual blocks of memory in the image frame buffer 50 are shown schematically in FIG. 3 as individual lines superimposed on each other. The image frame data from the image frame buffer 50 is accessed by a frame registrator 54, which determines the portion of each image frame the overlaps portions of other image frames. Image frames may be registered with other image frames through a variety of techniques, including those described in the previously cited application to Peterson et al.

After the image frames have been registered with each other by the frame registrator 54, the data corresponding to each image frame are stored in a history buffer 60 along with data identifying the relative spatial position of each image frame. Again, the history buffer 60 may be a dedicated memory, a portion of system memory used by the CPU 46, the same memory that is used as the image frame memory 50 or some other memory. The history buffer 60 stores the data corresponding to each image frame and its spatial position, in a depth in the illustrated embodiment of up to eight overlapping pixels at each pixel location. The individual blocks of memory in the history buffer 60 are shown schematically in FIG. 3 as individual lines staggered to show the overlap between adjacent image frames. The image frame data stored in the history buffer 60 are combined in accordance with associated translation and rotation parameters to form data corresponding to a panoramic image, and this panoramic image is applied to the video processor 26 for display (FIG. 2). As explained in greater detail below, the image frame data stored in the history buffer 60 and the extended image memory 42 may be accessed and manipulated by a trim/edit control 64. Alternatively, the trim/edit control 64 may access and manipulate data stored in the image frame memory 50 instead of or in addition to manipulating data stored in the history buffer 60 and extended image memory.

Figure 6A:
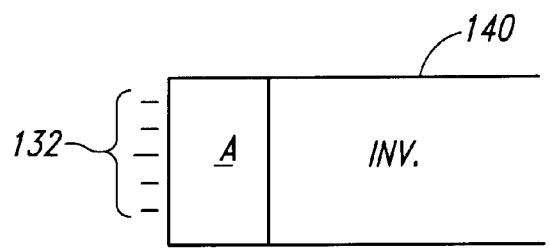
FIGS. 6a–6c are schematic views illustrating a technique for entering successive image frames into the history buffer used in the extended field of view image processor of FIG. 3.
Figure 6B:
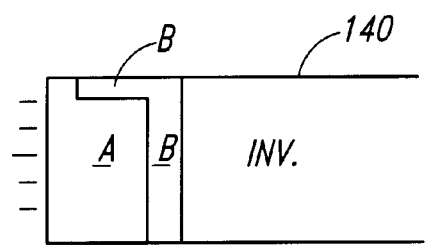
Figure 6C:
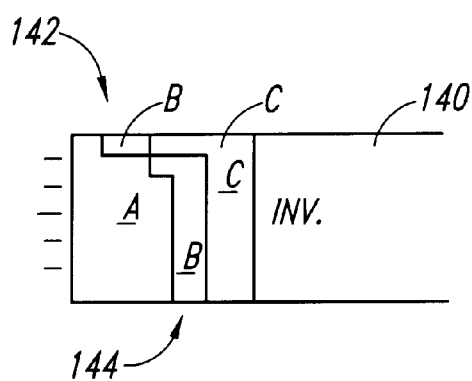

The manner in which data corresponding to individual image frames are registered and stored in the history buffer 60 will now be explained with reference to FIGS. 4a–6c. Referring, first, to FIG. 4a, three exemplary image frames A, B, and C are shown, which are acquired as the initial image frames for a panoramic image. Image frame A is the first to be acquired as the scanhead 10 moves from left to right to acquire image frames A, B, and C in succession. Image frame A is therefore entered first into the history buffer 60 as shown in FIG. 5. If the scanhead 10 were moving from right to left, the first image frame A would conceptually be aligned at the right side of the buffer 60 so that the panoramic image could extend from right to left instead of from left to right as depicted in this example. When data corresponding to the image frame A is entered into the history buffer 60, it may completely fill the pixel storage areas (depth z) beneath its x, y coordinates with image A pixel values as shown in FIG. 6a. FIGS. 6a–6c depict the history buffer cross-section in a plane 140 between arrows 6—6 in FIG. 5.

Image frame B is next acquired and aligned with image frame A as described above. Image frame B is stored in the history buffer 60 in its aligned position in x, y coordinates with respect to image frame A. Where image frame B overlays image frame A, the image frame A pixels are "pushed down" by one pixel depth so that the upper pixel is occupied by a pixel from image frame B and the remaining are still occupied by image frame A pixel values, as shown in FIG. 6b. In areas where image frame B does not overlay image frame A, the full pixel depth is filled with image frame B pixel values.

When image frame C is acquired and aligned with image frame B data, the push down process is repeated, as shown in FIG. 6c. In the columns indicated by arrow 142 where all three image frames overlap, the top pixel is from image frame C, the next pixel down is from image frame B, and the remaining pixel depth is filled with image frame A pixels. In image frame areas where only image frames B and C overlap, the top pixel in the column is an image frame C pixel, and those below are image frame B pixels. The above-described process continues as additional image frames are acquired to create the panoramic image. Although one technique for filling the history buffer 60 has been described herein, it will be understood that other techniques, both presently known and hereinafter developed, may be used.

Unlike prior art panoramic imaging systems, the data corresponding to each image frame is continuously stored in the imaging system 18, which, in the embodiment shown, is stored in both the image frame buffer 50 and in the history buffer 60. As mentioned above, the data stored in the history buffer 60 may be accessed by the trim/edit control 64 to eliminate data corresponding to selected image frames from the image frames that are used to form the panoramic image. The trim/edit control 64 may be implemented in hardware or it may be implemented in software executed by the CPU 46 or another processor included in the ultrasound imaging system 18. In the embodiment explained herein, the trim/edit control 64 is implemented in software, and it operates according to two distinct processes, namely an edit process and a trim process. In the edit process, data corresponding to specific image frames are eliminated from the image frame data used to form the panoramic image. In the trim process, data corresponding to portions of the panoramic mosaic extending beyond specific boundaries are eliminated from the extended image memory and the history buffer, either with or without modification of the frame buffer data. As a result, the trim process sets the end boundaries of the resulting panoramic image.

Figure 7:
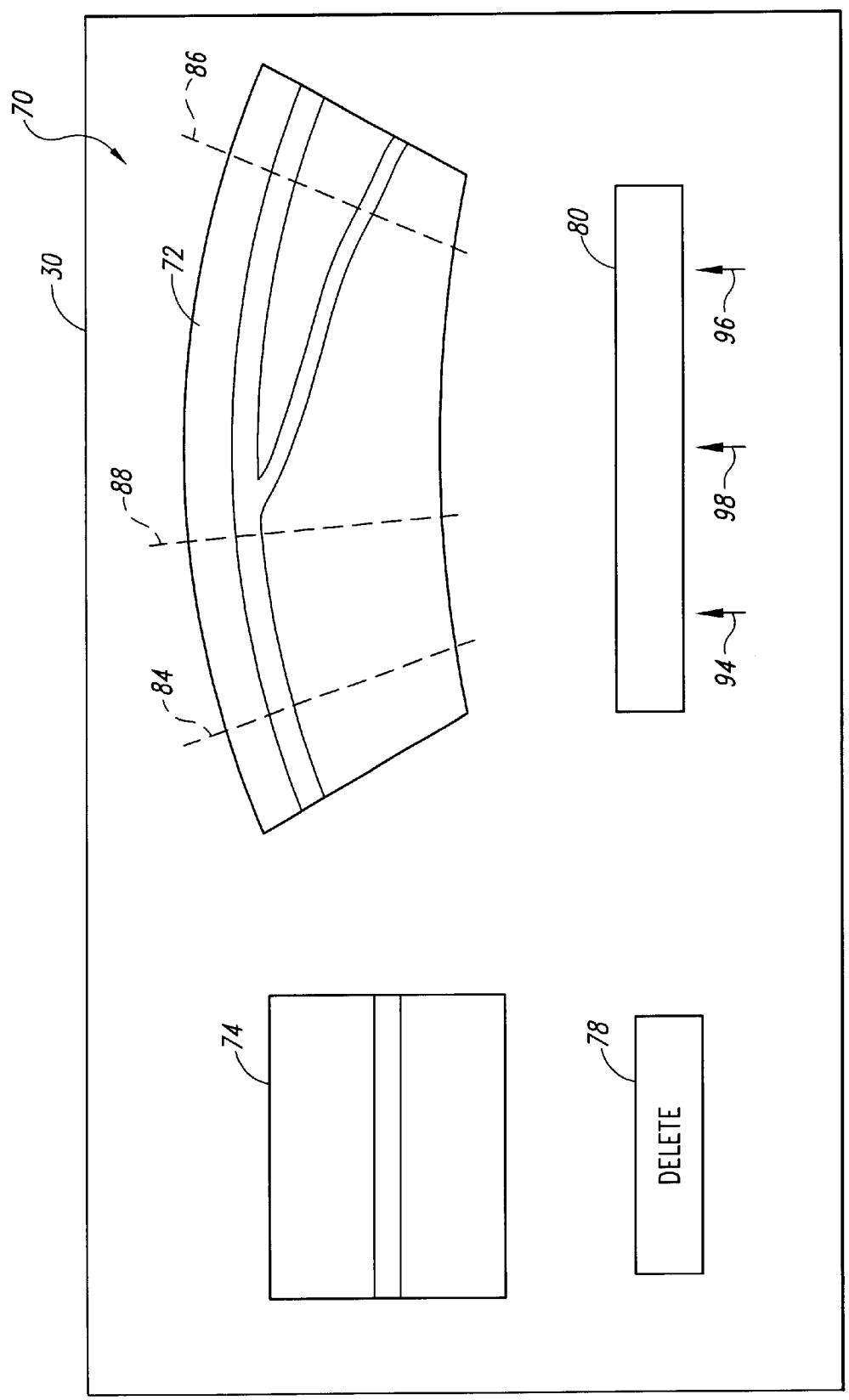
FIG. 7 is a screen display of one embodiment of a user interface for the panoramic ultrasonic diagnostic imaging system of FIG. 2.

One embodiment of a user interface 70 for the system 18 shown on the display 30 is illustrated in FIG. 7. The user interface 70 includes a display of the panoramic image 72, a display of an individual image frame 74, a "DELETE" softkey 78 positioned below the displayed image frame 74, and an index bar 80 displayed beneath the panoramic image 72. The panoramic image 72 is composed of a combination of currently selected image frames. The index bar 80 graphically represents the full extent of the image frame data corresponding to all of the saved image frames. Displayed on the panoramic image 72 are a left trim cursor 84, a right trim cursor 86, and an edit cursor 88, all of which are controllable by the user interface device 48 (FIG. 2). The position of the left trim cursor 84 is controlled to designate a desired left border of the panoramic image 72, the position of the right trim cursor 86 is controlled to designate a desired right border of the panoramic image 72, and the position of the edit cursor 88 is controlled to designate the location of an image frame that should be examined in greater detail, as described below. Displayed beneath the index bar 80 are left and right arrows, 94, 96, respectively, that designate the location of the right and left extent of the image frames used to make up the currently displayed panoramic image 72. Also displayed beneath the index bar is an image frame arrow 98 that identifies the relative position of the image frame 74 displayed on the left hand side of the screen 30.

In operation, the displayed panoramic image 72 is trimmed by manually adjusting the locations of the left trim cursor 84 and the right trim cursor 86. The system 18 then adjusts the left and right arrows 94, 96, respectively, beneath the index bar 80 to correspond to the positions of the cursors 84, 86, respectively, and eliminates any portion of any image frame from the panoramic image 72 having a position outside the range bordered by the arrows 84, 86. In the event the clinician decides to further trim the panoramic image 72, the cursors 84, 86 are readjusted, as described above. Significantly, since data corresponding to all of the image frames represented by the index bar 80 have been saved in the system 18, the positions of the cursors 84, 86 can subsequently be adjusted to extend the width of the displayed panoramic image 72. When the panoramic image 72 is trimmed, the scale of the image 72 is preferably increased so that the image 72 occupies substantially the same area as it did before being trimmed. However, if desired, the scale of the panoramic image 72 can remain the same before and after the trimming procedure described above.

In the editing process, the edit cursor 88 is adjusted to overlie an area of the panoramic image 72 that may be impaired by flash artifact or some other deficiency. The system 18 then adjusts the position of the edit arrow 98 to show the relative position of a selected image frame corresponding to the location of the edit cursor 88, and displays the selected image frame at 74. It will be understood that any position of the edit cursor 88 will normally overlies a portion of the panoramic image 72 made up of several image frames. However, the image frame selected by the edit cursor 88 can be the image frame centered beneath the cursor 88 or the image frame having a left edge closest to the cursor 88, for example. Using the user interface device 48 (FIG. 2), the clinician can adjust the edit cursor 88 or 98 to sequentially display each of the image frames at 74 until an image frame exhibiting flash artifact or some other defect is found. The clinician then uses the user interface device 48 to select the "DELETE" softkey 78. The system 18 then eliminates the image frame shown at 74 from the image frames making up the panoramic image 72. The effect of deleting the image frame can then be viewed in the panoramic image 72, and additional image frames that should be eliminated can be selected in the same manner.

In addition to deleting a selected image frame, the system 18 can additionally be adapted to process selected image frames in a selected manner. For example, the system 18 may use known techniques for improving the clarity of image frames.

As described above, the image frames to be eliminated during the editing process are selected manually after all of the image frames have been obtained and stored. Alternatively, the image frames to be eliminated during the editing process can be automatically selected either after all of the image frames have been obtained and stored or in real time as the image frames are being obtained. Accordingly, data corresponding to each of the image frames may be coupled from the image frame buffer to the trim/edit control through a data path shown by a dotted line in FIG. 3. The trim/edit control 64 then automatically examines each image frame using defined criteria. In the event an image frame exhibits flash artifact or some other defect or undesired characteristic, the system 18 automatically deletes data corresponding to the image frame from the history buffer 60. Alternatively, rather than deleting the image frame data from the history buffer 60, the system 18 may simply not transfer data corresponding to a defective image frame from the history buffer 60 to the extended image memory 42 or not transfer data corresponding to a defective image frame from the image frame buffer 50 to the history buffer 60. Consequently, the panoramic image 72 is composed only from image frames that do not exhibit flash artifact or some other defect.

In a manner similar to the previously described auto-edit procedure, the system 18 may also be programmed to perform an auto-trimming procedure. Accordingly, criteria is established to set the boundaries of the panoramic image 72. Each image frame is then automatically analyzed to identify and eliminate data corresponding to portions of image frames beyond the set boundaries. As with the auto-edit procedure, this auto-trimming procedure may be performed either after all of the image frames have been obtained and stored or in real time while the image frames are being obtained.

As mentioned above, the trim/edit control 64 and the user interface 70 are preferably implemented in software executed by the CPU 46 or some other processor. Appropriate programs for performing the editing and trimming processes described above can easily be provided by one skilled in the art of programming.

In contrast to the system 18 of the invention, in the prior art, the image frame data is incorporated into panoramic image data as each image frame is obtained. Consequently, data corresponding to each individual image frame is not retained, thereby making it impossible to eliminate a defective image frame from a panoramic image after the image frame has been obtained.

From the foregoing it will be appreciated that, although specific embodiments of the invention have been described herein for purposes of illustration, various modifications may be made without deviating from the spirit and scope of the invention. For example, although the system 18 stores data corresponding to each image frame, including defective image frames, in the image frame buffer 50, the extended image memory 42, and the history buffer 60, it will be understood that it need only be stored in the image frame buffer 50. If so, the trim/edit control will either selectively delete data from the image frame buffer 50 for defective image frames or prevent such data from being transferred to the extended image memory and the history buffer 60. The advantage of storing image frame data in the image frame buffer 50, the extended image memory 42, and the history buffer is the ability to display a modified panoramic image 72 without rebuilding the data stored in the extended image memory 42 and the history buffer 60 each time data corresponding to a defective image frame are eliminated. Also, of course, instead of having the trim/edit control 64 interface with the extended image memory 42 and the history buffer 60, the trim/edit control 64 may instead interface with the image frame buffer 50 even if image frame data are stored in the image frame buffer 50, the extended image memory 42, and the history buffer 60. Further, although data stored in the image frame buffer corresponding to defective image frames will generally not be used to form the panoramic image 72, such data may nevertheless be used by the frame correlator 54 to properly sequence the image frame data in the extended image memory 42 and the history buffer 60. Accordingly, the invention is not limited except as by the appended claims.

What is claimed is:

1. An ultrasound imaging system for generating a panoramic image, the system comprising:

a scanhead structured to generate an electrical signal corresponding to ultrasound echoes;

a beamformer coupled to the scanhead to generate electrical signals corresponding to ultrasound echoes from a beam beneath the scanhead;

a scan converter coupled to the beamformer to generate data corresponding to a plurality of image frames as the scanhead is scanned across a field of interest;

an image processor coupled to the scan converter, the image processor storing data corresponding to each of the image frames and retaining the image frame data after the panoramic image has been generated, the image processor being further structured to generate data corresponding to the panoramic image from data corresponding to selected image frames, the image processor comprising:

an image frame buffer coupled to the scan converter, the image frame buffer being structured to store data corresponding to each of the image frames;

a frame correlator coupled to the image frame buffer, the frame correlator being structured to determine the relative spatial relations of each of the image frames and to generation spatial relation data corresponding thereto;

a history buffer coupled to the frame correlator, the history buffer being structured to store the data corresponding to each of the image frames and associated spatial position data;

an image frame selector coupled to one of the image frame buffer and the history buffer, the image frame selector being structured to select data corresponding to image frames that are to be excluded from inclusion in the data corresponding to the panoramic image;

an image memory coupled to the image frame selector, the image memory storing the data corresponding to the panoramic image; and a display coupled to the image memory, the display generating the panoramic image.

2. The ultrasound imaging system of claim 1 wherein the image frame selector is structured to select data corresponding to image frames that are to be excluded from inclusion in the data corresponding to the panoramic image as the data corresponding to the image frames are being generated.

3. The ultrasound imaging system of claim 2 wherein the image frame selector is structured to automatically select data corresponding to image frames that are to be excluded from inclusion in the data corresponding to the panoramic image in accordance with predetermined selection criteria.

4. The ultrasound imaging system of claim 1 wherein the image frame selector is structured to select data corresponding to image frames that are to be excluded from inclusion in the data corresponding to the panoramic image after all of the data corresponding to the image frames has been generated and stored in the image frame buffer.

5. The ultrasound imaging system of claim 1 wherein the image frame selector is coupled to the history buffer.

6. The ultrasound imaging system of claim 1 wherein the image frame selector comprises a user interface to allow a user to select the data to be excluded from the panoramic image without examining corresponding frames of the image frame buffer.

7. The ultrasound imaging system of claim 1 wherein the image frame selector comprises a user interface to allow a user to select the data corresponding to image frames that are to be excluded from inclusion in the data corresponding to the panoramic image.

8. The ultrasound imaging system of claim 7 wherein the user interface comprises:

a panoramic image shown on the display;

an edit cursor superimposed on the panoramic image; and an image frame shown on the display, the displayed image frame being an image frame used to form a portion of the panoramic image that the edit cursor overlies so that the position of the edit cursor on the displayed panoramic image selects the displayed image frame.

9. The ultrasound imaging system of claim 8 wherein the user interface further comprises:

an index bar representing the temporal extent of the image frames for which data is stored in the image frame buffer; and an index bar cursor positioned along the index bar, the position of the index bar cursor on the index bar corresponding to the relative spatial position of the displayed image frame.

10. The ultrasound imaging system of claim 8 wherein the user interface further comprises a delete selector actuatable to cause data corresponding to the displayed image frame to be eliminated from data corresponding to the displayed panoramic image.

11. The ultrasound imaging system of claim 10 wherein the delete selector comprises a delete softkey shown on the display.

12. The ultrasound imaging system of claim 7 wherein the user interface comprises:

an index bar representing the temporal extent of the image frames for which data is stored in the image frame buffer; and an index bar cursor positioned along the index bar, the position of the index bar cursor on the index bar corresponding to the relative spatial position of the displayed image frame.

13. The ultrasound imaging system of claim 7 wherein the user interface comprises:

a panoramic image shown on the display;

a left trim cursor superimposed on the panoramic image toward the left side of the panoramic image; and a right trim cursor superimposed on the panoramic image toward the right side of the panoramic image, the left and right trim cursor causing data corresponding to portions of image frames outside the range between the left and right trim cursors to be excluded from inclusion in the data corresponding to the panoramic image.

14. In an ultrasound imaging system structured to display a panoramic image on a display, the panoramic image being formed from a plurality of partially spatially overlapping image frames, a user interface, comprising:

an edit cursor superimposed on the panoramic image;

an image frame shown on the display, the displayed image frame being an image frame used to form a portion of the panoramic image that the edit cursor overlies so that the position of the edit cursor on the displayed panoramic image selects the displayed image frame;

an index bar representing the temporal extent of the image frames; and an index bar cursor positioned along the index bar, the position of the index bar cursor on the index bar corresponding to the relative spatial position of the displayed image frame.

15. The user interface of claim 14, further comprising a delete selector actuatable to cause the displayed image frame to be eliminated from the imaged frames forming the displayed panoramic image.

16. The user interface of claim 15 wherein the delete selector comprises a delete softkey shown on the display.

17. In an ultrasound imaging system structured to display a panoramic image on a display, the panoramic image being formed from a plurality of partially spatially overlapping image frames generated during use of the ultrasound imaging system, a user interface, comprising:

an image frame displayed on the display;

an index bar representing the spatio-temporal extent of all of the image frames; and an index bar cursor positioned along the index bar, the position of the index bar cursor on the index bar corresponding to the relative spatial position of the displayed image frame.

18. In an ultrasound imaging system structured to display a panoramic image on a display, the panoramic image being formed from a plurality of partially spatially overlapping image frames generated during use of the ultrasound imaging system, a user interface, comprising:

a left trim cursor superimposed on the panoramic image toward the left side of the panoramic image; and a right trim cursor superimposed on the panoramic image toward the right side of the panoramic image, the left and right trim cursor selecting portions of image frames that are outside the range between the left and right trim cursors that are to be excluded from inclusion in the image frames forming the displayed panoramic image.

19. In an ultrasound imaging system structured to display a panoramic image on a display, the panoramic image being formed from a plurality of partially spatially overlapping image frames generated during use of the ultrasound imaging system, a user interface comprising a selector interface allowing a user to select specific image frames to be excluded from the image frames forming the displayed panoramic image.

20. The user interface of claim 19, wherein the selector interface comprises:

an image frame selector structured to select a specific image frame, the selected image frame being displayed on the display; and a delete selector actuatable to cause the displayed image frame to be eliminated from the image frames forming the displayed panoramic image.

21. The user interface of claim 20 wherein the delete selector comprises a delete softkey shown on the display.

22. The user interface of claim 20 wherein the image frame selector comprises a cursor superimposed on the panoramic image, the cursor overlies a portion of the displayed panoramic image formed by a specific image frame so that the position of the cursor on the displayed panoramic image determines the selected image frame.

23. In an ultrasound imaging system, a method of displaying a panoramic image, comprising:

acquiring a sequence of partially spatially overlapping image frames;

storing data corresponding to the image frames;

combining at least some of the data corresponding to a plurality of the image frames to provide data corresponding to a panoramic image;

displaying an image from the data corresponding to a panoramic image;

continuing to store the data corresponding to the image frames after the panoramic image has been displayed; and selectively excluding the data corresponding to at least one image frame from the data corresponding to the displayed panoramic image.

24. The method of claim 23 wherein the act of selectively excluding the data corresponding to the at least one image frame comprises automatically selecting the data corresponding to the at least image frame that are to be excluded from inclusion in the data corresponding to the panoramic image in accordance with predetermined selection criteria.

25. The method of claim 24 wherein the act of automatically selecting the data corresponding to the at least one image frame that are to be excluded from inclusion in the data corresponding to the panoramic image comprises automatically selecting the data corresponding to the at least one image frame that is to be excluded from inclusion in the data corresponding to the panoramic image after the data corresponding to the image frames has been stored.

26. The method of claim 24 wherein the act of automatically selecting the data corresponding to the at least one image frame that are to be excluded from inclusion in the data corresponding to the panoramic image comprises automatically selecting the data corresponding to the at least one image frame that is to be excluded from inclusion in the data corresponding to the panoramic image while the image frames are being acquired.

27. The method of claim 23 wherein the act of selectively excluding the data corresponding to the at least one image frame comprises:

reviewing data associated with at least one of the image frames to determine if the data corresponding to the reviewed image frame should be excluded from the data corresponding to the displayed panoramic image; and manually excluding data corresponding to the reviewed image frame from the data corresponding to the displayed panoramic image.

28. The method of claim 27 wherein the act of manually excluding data corresponding to the reviewed image frame from the data corresponding to the displayed panoramic image comprises actuating a delete key.

29. The method of claim 27 wherein the act of reviewing at least one of the image frames comprises:

superimposing a cursor on the panoramic image, the position of the cursor on the panoramic image being controlled by a user; and displaying for review an image frame used to form a portion of the panoramic image that the edit cursor overlies so that the position of the edit cursor on the displayed panoramic image selects the image frame to be reviewed.

30. The method of claim 29, further comprising:

displaying an index bar representing the spatial extent of the image frames for which data is stored; and positioning an index bar cursor along the index bar, the position of the index bar cursor on the index bar corresponding to the relative spatial position of the displayed image frame.

31. The method of claim 23 wherein the act of selectively excluding the data corresponding to the at least one image frame comprises:

superimposing a left trim cursor on the panoramic image toward the left side of the panoramic image;

superimposing a right trim cursor superimposed on the panoramic image toward the right side of the panoramic image; and excluding data corresponding to portions of image frames outside the range between the left and right trim cursors from inclusion in the data corresponding to the panoramic image.

32. In an ultrasound imaging system, a method of displaying a panoramic image formed from a plurality of partially spatially overlapping image frames, the method comprising selecting specific image frames to be excluded from the image frames forming the displayed panoramic image.

33. The method of claim 32, further comprising storing data corresponding to the image frames and continuing to store the data corresponding to the image frames after the panoramic image has been displayed.

34. The method of claim 32 wherein the act of selecting specific image frames to be excluded from the image frames forming the displayed panoramic image comprises automatically selecting specific image frames to be excluded according to predetermined criteria.

35. The method of claim 34 wherein the act of automatically selecting specific image frames to be excluded comprises automatically selecting specific image frames to be excluded after all of the image frames have been obtained.

36. The method of claim 34 wherein the act of automatically selecting specific image frames to be excluded comprises automatically selecting specific image frames to be excluded in essentially real time as the image frames are being obtained.

37. A The method of claim 32 wherein the act of selecting specific image frames to be excluded from the image frames forming the displayed panoramic image comprises:

selecting a specific image frame for review;

reviewing the selected image frame to determine if the selected image frame should be excluded from the image frames forming the displayed panoramic image; and manually excluding the reviewed image frame from the image frames forming the displayed panoramic image.

38. The method of claim 37 wherein the act of selecting a specific image frame for review comprises positioning a cursor over the displayed panoramic image, the cursor overlying a portion of the panoramic image formed by the selected image frame.

39. The method of claim 37 wherein the act of manually excluding the reviewed image frame from the image frames forming the displayed panoramic image comprises manually actuating a delete key.

* * * * *